United States Patent
Gadgil et al.

(10) Patent No.: US 7,217,933 B2
(45) Date of Patent: *May 15, 2007

(54) UV WATER DISINFECTOR

(75) Inventors: Ashok Gadgil, El Cerrito, CA (US); Eduardas Kazakevicius, Vilnius (LT); Anushka Drescher, Berkeley, CA (US)

(73) Assignee: WaterHealth International, Inc., Lake Forest, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/302,417

(22) Filed: Dec. 12, 2005

(65) Prior Publication Data

US 2006/0192136 A1 Aug. 31, 2006

Related U.S. Application Data

(63) Continuation of application No. 10/982,857, filed on Oct. 12, 2004, now Pat. No. 6,974,958, which is a continuation of application No. 10/043,647, filed on Jan. 10, 2002, now Pat. No. 6,803,587.

(60) Provisional application No. 60/261,120, filed on Jan. 11, 2001.

(51) Int. Cl.
*A61L 1/10* (2006.01)

(52) U.S. Cl. .................. 250/423 R; 250/434; 250/428; 250/435

(58) Field of Classification Search ...................... None
See application file for complete search history.

(56) References Cited

U.S. PATENT DOCUMENTS

| | | |
|---|---|---|
| 2,504,349 A | 4/1950 | Prieto |
| 3,491,234 A | 1/1970 | Wiltrout |
| 3,562,520 A | 2/1971 | Hippen |
| 3,710,111 A | 1/1973 | Collura |
| 3,836,781 A | 9/1974 | Ellison |

(Continued)

OTHER PUBLICATIONS

Luckiesh, D.Sc., D.E., Matthew, Applications of Germicidal, Erythemal and Infrared Energy, Van Nostrand Co., Inc., New York, NY, 1946, pp. Foreword, 231-269, 441-451.

(Continued)

*Primary Examiner*—Nikita Wells
(74) *Attorney, Agent, or Firm*—Knobbe Martens Olson & Bear LLP

(57) ABSTRACT

A device that permits the in-home UV treatment of drinking water such as tap water is disclosed. The device employs a bare low-energy UV lamp suspended below a reflector and above a free surface of water flowing within the device. The water is supplied from a tap or other store of drinking water and proceeds through the device by the force of gravity. The device itself is not pressurized. The flow of water within the device is exposed to UV radiation from the UV lamp and is disinfected as a result. In the illustrated embodiment, the device is of a small size to permit its use, for example, directly at a tap for drinking water within the home. The flow rate of the device is commensurate with the normal flow rate of tap water, preferably less than about 8 liters per minute. The lamp power for safely disinfecting the water can be less than 20 watts, and in the illustrated embodiment the lamp is a low-pressure Hg lamp.

20 Claims, 2 Drawing Sheets

U.S. PATENT DOCUMENTS

| | | |
|---|---|---|
| 3,858,048 A | 12/1974 | Shand et al. |
| 4,102,645 A | 7/1978 | Meacham, Jr. et al. |
| 4,201,916 A | 5/1980 | Ellner |
| 4,304,996 A | 12/1981 | Blades |
| 4,622,465 A | 11/1986 | Harig et al. |
| 4,629,896 A | 12/1986 | Bridgen |
| 4,661,264 A | 4/1987 | Goudy, Jr. |
| 4,742,231 A | 5/1988 | Bridgen |
| 4,899,057 A | 2/1990 | Koji |
| 4,909,931 A | 3/1990 | Bibi |
| 5,186,830 A | 2/1993 | Rait |
| 5,217,607 A | 6/1993 | Dalton, III et al. |
| 5,227,053 A | 7/1993 | Brym |
| 5,230,792 A | 7/1993 | Sauska et al. |
| RE34,513 E | 1/1994 | Ellner |
| 5,288,412 A | 2/1994 | Voorhees et al. |
| 5,366,705 A | 11/1994 | Reidy |
| 5,387,804 A | 2/1995 | Suzuki et al. |
| 5,420,432 A | 5/1995 | Manook et al. |
| 5,441,179 A | 8/1995 | Marsh |
| 5,503,800 A | 4/1996 | Free |
| 5,536,403 A | 7/1996 | Sugimoto |
| 5,584,990 A | 12/1996 | Sugimoto |
| 5,597,482 A | 1/1997 | Melyon |
| 5,597,487 A | 1/1997 | Vogel et al. |
| 5,628,895 A | 5/1997 | Zucholl |
| 5,632,890 A | 5/1997 | Sugimoto |
| 5,635,133 A | 6/1997 | Glazman |
| 5,660,719 A | 8/1997 | Kurtz et al. |
| 5,725,762 A | 3/1998 | Beal et al. |
| 5,780,860 A | 7/1998 | Gadgil et al. |
| 5,843,304 A | 12/1998 | Marchesseault et al. |
| 5,843,309 A | 12/1998 | Mancil |
| 5,877,392 A | 3/1999 | Russell et al. |
| 5,900,212 A | 5/1999 | Maiden et al. |
| 5,951,876 A | 9/1999 | Snowball |
| 6,031,241 A | 2/2000 | Silfvast et al. |
| 6,129,893 A | 10/2000 | Bolton et al. |
| 6,156,210 A | 12/2000 | Sadkhin |
| 6,565,803 B1 | 5/2003 | Bolton et al. |
| 6,803,587 B2 * | 10/2004 | Gadgil et al. ............... 250/434 |
| 6,974,958 B2 * | 12/2005 | Gadgil et al. ............... 250/434 |

OTHER PUBLICATIONS

Drescher et al., "Cryptosporidium Inactivation By Low Pressure UV In A Water Disinfection Device," *Journal of Environmental Health*, vol. 64, No. 3, pp. 31-35 (Oct. 2001).

Connelly et al., "Refinement and Field Testing of a Low Cost UV Water Disinfection System for Household Use in Lesser-Developed Nations", Research Proposal, Feb. 18, 2000, pp. 1-18, Berkeley, CA, http://www.nextnvention.com/UV/final_poster-small_version.doc (last visited Dec. 8, 2005).

Connelly, "Refinement and Filed Testing of a Low Cost UV Water Disinfection System for Household Use in Lesser-Developed Nations", Expanded Proposal Form for Development Marketplace, proposal apparently "due" Jan. 14, 2000, Albany, CA, http://www.nextnvention.com/UV/UV-Tube_PROPOSAL_2-18-00_rev.doc (last visited Dec. 8, 2005).

Terrado et al., "The UV-Tube Affordable Water Disinfection for Household Use", World Bank Development Marketplace Poster Presentaton, Feb. 7-8, 2000, http://www.nextnvention.com/UV/World_Bank_Proposal.doc (last visited Dec. 8, 2005).

* cited by examiner

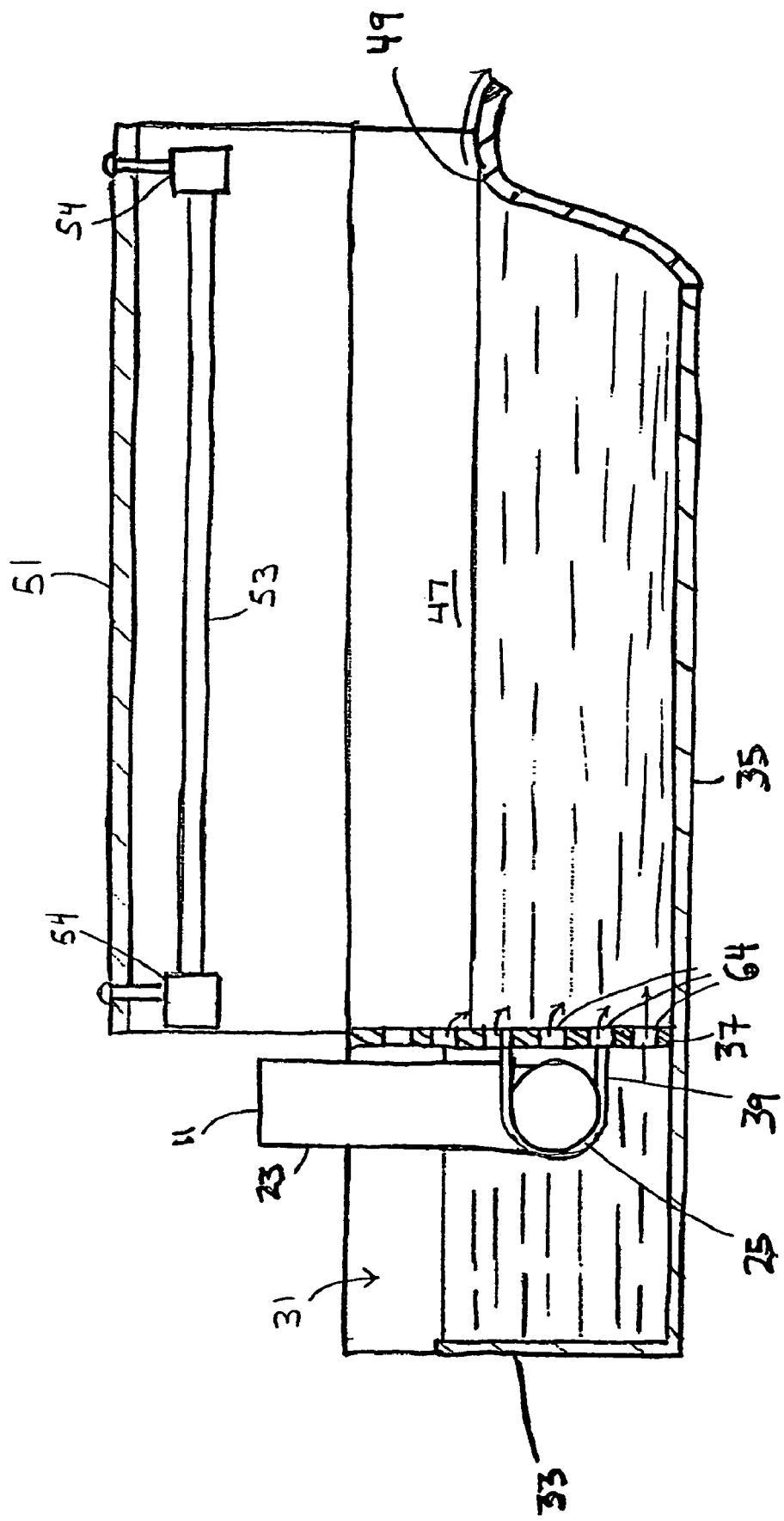

UV WATER DISINFECTOR

REFERENCE TO RELATED APPLICATION

This application is a continuation of U.S. application Ser. No. 10/982,857, filed Oct. 12, 2004, issuing Dec. 13, 2005 as U.S. Pat. No. 6,974,958, which is a continuation of U.S. application Ser. No. 10/043,647, filed Jan. 10, 2002, issued Oct. 12, 2004 as U.S. Pat. No. 6,803,587, which claims the priority benefit under 35 U.S.C. § 119(e) to provisional application No. 60/261,120, filed Jan. 11, 2001.

BACKGROUND OF THE INVENTION

1. Field of the Invention

The present invention is related to the UV disinfection of water and other liquid streams. In particular, the present invention provides a UV disinfector for use in the disinfection of tap water and other sources of drinking water used in the home.

2. Description of the Related Art

Methods used heretofore to disinfect water include the use of chlorine and other chemical agents as well as irradiation. However, certain pathogenic organisms, such as *Cryptosporidium parvum*, are resistant to chemical-based disinfection. Additionally, organisms such as *Cryptosporidium*, which are present in most municipal drinking water systems, have recently been shown to present a significant health risk to immunocompromised individuals even at the very low levels at which such pathogens are present in municipal drinking water.

SUMMARY OF THE INVENTION

The UV water disinfector of the present invention provides a simple solution to the problems described above in that it is a device that permits the in-home UV treatment of drinking water such as tap water. The device of the preferred embodiment employs a bare low-energy UV lamp suspended above a free surface of water flowing within the device. The water is supplied from a tap or other store of drinking water and proceeds through the device by the force of gravity. The device itself is not pressurized. The flow of water within the device is exposed to UV radiation from the UV lamp and is disinfected as a result.

In the illustrated embodiment, the device is of a small size to permit its use, for example, directly at a tap for drinking water within the home. The flow rate of the device is commensurate with the normal flow rate of tap water, preferably less than about 8 liters per minute. The lamp power for safely disinfecting the water can be less than 20 watts, and in the illustrated embodiment the lamp is a low-pressure Hg lamp.

BRIEF DESCRIPTION OF THE DRAWINGS

FIG. 2 is a side cross-sectional view of the UV disinfector of the same embodiment.

DETAILED DESCRIPTION OF THE PREFERRED EMBODIMENT

Figure 1:
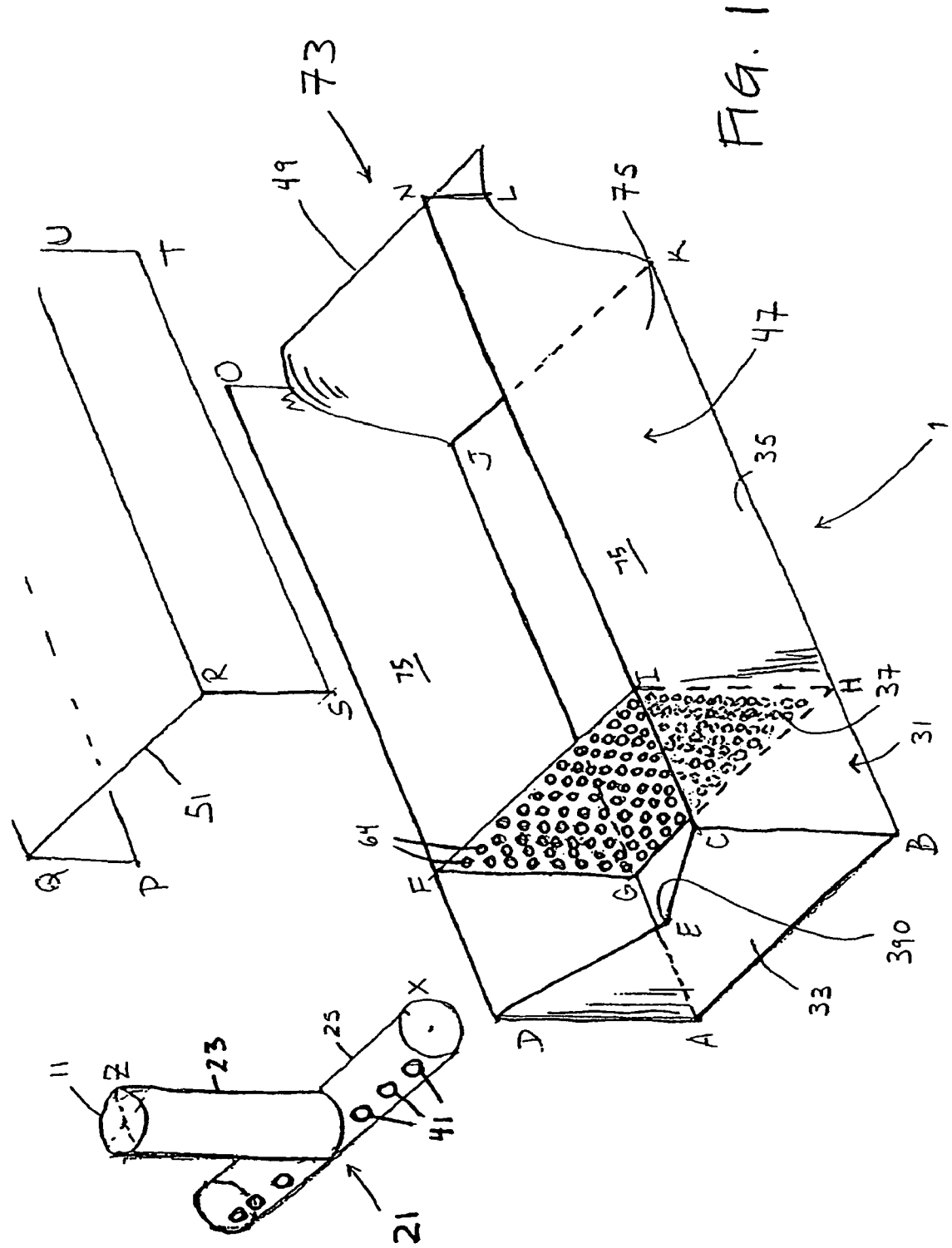
FIG. 1 is an exploded perspective view depicting the UV disinfector of an embodiment of the present invention.

FIG. 1 depicts a UV water disinfector 1 in accordance with an embodiment of the present invention. A main water tray 73, inlet manifold 21, and upper reflector 51 are shown in FIG. 1. The water disinfector 1 also includes an outer casing (not shown). The disinfector 1 includes many features and advantages generally described in U.S. Pat. No. 5,780,860, issued Jul. 14, 1998, the disclosure of which is incorporated herein by reference. However, the disinfector 1 is particularly adapted (e.g., in size, power, flow rate, etc.) to use in the home for disinfecting municipal water that is generally considered safer for drinking. For example, the portions of water disinfector 1 shown in FIG. 1 preferably have a length of about 48 cm or less, a width of about 19.5 cm or less, and a height of about 15.75 cm or less; more preferably have a length of about 40 cm or less, a width of about 16.25 cm or less, and a height of about 13.125 cm or less; even more preferably have an overall length within a range of about 35.2–28.8 cm, a width within a range of about 14.3–11.7 cm, and a height within a range of about 11.55–9.45 cm; and most preferably have an overall length of approximately 32 cm, a width of about 13 cm, and a height of about 10.5 cm. Such a small size is well adapted to in-home use, such as in a kitchen sink or a counter adjacent thereto.

Furthermore, unlike many prior art devices, the UV water disinfector 1 in accordance with the present embodiment is not pressurized and involves no pumping of the water as it is being treated. The water passes through the treatment chamber as a result of gravity.

Referring to FIGS. 1 and 2, an inlet port 11 that is adapted to be connected to a common household tap, or a holding tank fed by tap water, protrudes into an inlet chamber 31. The feed water enters the UV disinfector 1 through the inlet port 11 by the pressure from the tap. The inlet port 11 enters an inlet manifold 21, which is comprised of a vertical inlet feed tube 23 which connects to a horizontal inlet distribution tube 25, both of which have a diameter of approximately 1.5 cm and which comprise food-grade plastic such as polypropylene. Thus, the inlet manifold 21 forms an inverted T configuration. The inlet feed tube 23 enters the UV disinfector 1 from above. As an option, a solenoid shut off valve can be provided in the inlet feed tube 23. The solenoid valve will stop the flow of feed water into the UV disinfector if there is a stoppage of power to the UV disinfector, as described in U.S. Pat. No. 5,780,860.

The bulk of the inlet manifold 21 is positioned in the inlet chamber 31. The inlet chamber 31 is defined by a main tray inlet wall 33 (about 9 cm by 5 cm), a main tray floor 35, and a baffle wall 37 (about 9 cm by 5 cm). There is about a 6 cm separation between the main tray inlet wall 33 and the baffle wall 37. The inlet feed tube 23 typically abuts the baffle wall 37. The inlet distribution tube 25 typically rests directly on the sides of main tray floor 35, providing for considerable stability. Additionally, the inlet distribution tube 25 can be attached to the baffle wall 37 by ring attachments 39. The distribution tube 25 is provided with distribution tube holes 41, which provide a flow-through of feed water into inlet chamber 31. These distribution tube holes 41 are typically 5 mm in diameter and are spaced at intervals of 1 cm from the center of one hole to the center of the neighboring hole. In addition, although not depicted in the Figures, a smaller hole having a diameter of approximately 2 mm is provided at the opposite side of distribution tube 25 from the distribution tube holes 41 and centered so as to be aligned with the vertical inlet feed tube 23. This hole serves to reduce the turbulence of the water flow into the inlet chamber 31.

The regulation of the water flow entering the UV disinfector 1 is provided by adapting the inlet port 11 to the type of tap employed. If, however, too much water should enter inlet chamber 31, the main tray inlet wall 33 is provided with a notch 390 so that feed water will overflow this wall rather than overflowing the baffle wall 37. The low point of the notch 390 is thus below the height of the baffle wall 37 and in the illustrated embodiment is approximately 3.4 cm above the main tray floor 35. This excess feed water falls to an outer casing bottom (not shown), where it drains away through a gap.

A treatment chamber 47 is defined by the baffle wall 37, the main tray floor 35, a curved outlet baffle dam 49, and a top reflector 51. When installed, the top reflector 51 overlaps the main tray by approximately 5 mm. The top reflector 51 houses a UV lamp 53 that is seated in a socket 54. The socket 54, in turn, is attached to the top reflector 51 by socket attachment bolts. Thus, the top reflector 51 supports and suspends the UV lamp 53 above the treatment chamber 47.

A power source and shut off relay provide the power to UV lamp 53 through a lamp circuit and ballast (not shown). The power source and shut off relay can be additionally connected to a solenoid shutoff valve, as mentioned.

The main tray floor 35 rests directly on an outer casing base that is not depicted in the Figures. The main tray floor 35 is angled to direct the laminar flow of the feed water that is produced by the baffle wall 37. The main tray is constructed of stainless steel having a UV reflectance of approximately 30%, while the top reflector is constructed of polished aluminum, having a UV reflectance in a range of approximately 75–80%.

In operation, the top reflector 51 recaptures otherwise lost UV light from the top of UV lamp 53, directing it back to the laminar flow. The feed water traverses the treatment chamber 47, and then cascades over outlet baffle dam 49, after which it is collected by a suitable collection device (not shown) for use as drinking water. Working in concert, these various features of the treatment chamber 47 ensure that the feed water directed in the laminar flow typically receives a similar dosage of UV radiation wherever it is positioned in the treatment chamber 47. This dosage is preferably within a range of 110–150 $mJ/cm^2$, more preferably within a range of 115–125 $mJ/cm^2$, and most preferably approximately 120 $mJ/cm^2$ under ideal conditions (water with turbidity of less than 1 NTU and a UV transmittance of more than 95% at 1 cm).

A suitable outlet box or other device such as a tap or the like, not depicted in the Figures, receives the treated water as it cascades over the outlet baffle dam 49, the top of which is approximately 3 cm above the main tray floor 35.

The UV lamp preferably consumes 25 watts or less, more preferably about 20 watts or less, even more preferably about 8–15 watts, and most preferably about 9–10 watts. This is considerably less power than that consumed by conventional water treatment devices. In other arrangements, the UV lamp may be a medium pressure lamp, which outputs broadband UV radiation, which is defined herein as UV radiation exhibiting a broad peak centered at about 500 nm, with the spectrum ranging from 250 nm to 800 nm. U.S. Pat. No. 6,129,893 to Bolton et al. discloses that such broadband UV radiation is capable of preventing replication in *Cryptosporidium parvum*. In the preferred embodiment, however, the lamp is a low pressure lamp, which outputs narrow-band UV radiation, which is defined herein as UV radiation exhibiting a narrow peak centered at 253.7 nm, with the width at one-half maximum intensity of less than 1 nm on either side of the center at 253.7 nm.

The use of narrow-band UV radiation has been shown by the present inventors to inactivate *Cryptosporidium parvum* oocysts, as described in Drescher et al., "*Cryptosporidium* Inactivation by Low Pressure UV in a Water Disinfection Device," *Journal of Environmental Health*, Vol. 64, No. 3, pp. 31–35 (October 2001), the disclosure of which is incorporated herein in its entirety. In brief, the inventors determined that when water containing a high level of live oocysts of *Cryptosporidium parvum* (which is one of the pathogens posing a health risk to immunocompromised individuals) was irradiated with narrow-band UV at a dosage of 120 $mJ/cm^2$, mice which ingested the treated water showed no signs of infection by the pathogen one week after ingestion. The infectivity of the oocysts was reduced by at least 5.4 orders of magnitude as a result of the narrow-band UV treatment. It is thus apparent that this narrow-band UV treatment is highly effective in the inactivation of these pathogens.

Prior art quartz sleeve protectors for UV lamp 53 are eliminated in the present design because the UV lamp 53 is carefully air-suspended above the flow of the feed water, and also because the UV lamp 53 burns at a sufficient temperature that condensation never develops at its surface. Both the failure of moisture requirements and the heavy UV bombardment avoids the problems of biomass buildup which plagued prior art configurations.

The baffle wall 37 rises from the main tray floor 35 extending along the main tray walls 75 upwards to the top edge thereof. The baffle wall 37 serves to position the feed water so as to provide a narrow distribution of UV dosages. However, the baffle wall 37 does not limit the height of the feed water. The height of the feed water as it traverses the UV disinfector 1 is limited to the height of the main tray walls 75.

The ultimate regulator of the feed water level during processing in UV disinfector 1 is outlet baffle dam 49, which rises only partway to the top of the main tray walls 75. The main tray unit 73 is made about 2 cm smaller than the outer casing (not depicted in the Figures), so there is considerable room for overflow to escape the main tray 73.

In the perspective view of FIG. 1, it can be seen that the baffle wall 37 is provided with baffle wall holes 64 about 0.3 cm in diameter, and spaced evenly about 0.6 cm apart from center to center. These serve to laminarize the flow of the feed water into treatment chamber 47 as shown in FIGS. 1 and 2.

It should be noted that these baffle wall holes 64, along with the small 2 mm hole in the intake manifold 21, are preferably the smallest holes through which the feed water passes in the disinfector of the present embodiment; no upstream or downstream filters are provided. This arrangement allows a flow rate appropriate for a household tap to be maintained even though the disinfector as a whole is quite small. In other arrangements, upstream or downstream filters may also be provided.

The gravity-driven feed rate of the water through treatment chamber 47 is preferably 8 liters per minute or less, more preferably about 4 liters per minute or less, even more preferably within a range of about 1–3 liters per minute, and most preferably approximately about 2 liters per minute.

The UV water disinfector described above is used in the following manner. First, the inlet port 11 is connected to a household tap, and power is supplied to the UV lamp. Next, the tap is opened, and water enters the inlet manifold 21 as a result of the tap pressure, passes through the holes provided in the inlet manifold 21, and enters inlet chamber 31. Next, this water is channeled in a laminar flow through the baffle wall holes 64 and enters treatment chamber 47, where it is subjected to a dose of UV sufficient to inactivate pathogenic organisms and disinfect the water. Finally, the disinfected water passes over outlet baffle dam 49 and is collected by a suitable collection device for use as drinking water.

Although the forgoing invention has been described in terms of a certain preferred embodiment, other embodiments will become apparent to those of ordinary skill in the art in view of the disclosure herein. Accordingly, the present invention is not intended to be limited by the recitation of preferred embodiments, but is intended to be defined solely by reference to the appended claims.

We claim:

1. An ultraviolet (UV) water disinfector, comprising:
   a feed water delivery system, wherein the feed water delivery system comprises a water inlet feed tube;
   an air-suspended UV lamp capable of providing narrowband UV radiation sufficient to inactivate *Cryptosporidium parvum* oocysts, and
   a treatment chamber beneath the UV lamp, wherein water is driven by gravity at a flow rate of 8 liters per minute or less.

2. The UV water disinfector of claim 1, further comprising a notch in said treatment chamber adapted to allow excess water to overflow, and an outer shell adapted to collect water which overflows.

3. The UV water disinfector of claim 1, wherein the UV lamp is adapted to provide narrowband UV radiation at a dosage of about 120 mJ/cm$^2$.

4. The UV water disinfector of claim 3, wherein the UV lamp uses less than 25 watts of power.

5. The UV water disinfector of claim 4, wherein the UV lamp uses less than about 20 watts of power.

6. The UV water disinfector of claim 5, wherein the UV lamp uses about 8–15 watts of power.

7. The UV water disinfector of claim 1, wherein the feed water delivery system has a flow rate of about 4 liters per minute or less.

8. The UV water disinfector of claim 1, wherein the feed water delivery system has a flow rate within a range of about 1–3 liters per minute.

9. The UV water disinfector of claim 1, having a length of about 48 cm or less, a width of about 19.5 cm or less, and a height of about 15.75 cm or less.

10. The UV water disinfector of claim 1, having a length of 40 cm or less, a width of 16.25 cm or less, and a height of 13.125 cm or less.

11. The UV water disinfector of claim 1, having a length within a range of about 35.2–28.8 cm, a width within a range of about 14.3–11.7 cm, and a height within a range of about 11.55–9.45 cm.

12. An ultraviolet (UV) water disinfector, comprising:
    a feed water delivery system, wherein the feed water delivery system comprises a water inlet feed tube;
    an air-suspended UV lamp using 20 watts of power or less, the UV lamp capable of providing narrowband UV radiation sufficient to inactivate *Cryptosporidium parvum* oocysts, and
    a treatment chamber beneath the UV lamp; wherein the feed water delivery system and the treatment chamber are configured to deliver water, under the influence of gravity, at a rate of less than about 8 liters per minute.

13. The UV water disinfector of claim 12, wherein the UV lamp comprises a low pressure mercury lamp.

14. The UV disinfector of claim 12, having a length of about 40 cm or less, a width of about 16.25 cm or less and a height of about 13.125 cm or less.

15. A method of disinfecting household tap water in a UV water disinfector, comprising:
    delivering household tap water to a feed water delivery system,
    flowing the household tap water from the feed water delivery system into a treatment chamber, wherein the water flowing into the treatment chamber is driven by gravity at a flow rate of 8 liters per minute or less, and
    disinfecting the household tap water by providing narrowband UV radiation from an air-suspended UV lamp over the treatment chamber, wherein the narrowband UV radiation is sufficient to inactivate *Cryptosporidium parvum* oocysts, and wherein the UV lamp uses less than 20 watts of power.

16. The method of claim 15, wherein the UV lamp uses less than 15 watts of power.

17. The method of claim 15, wherein the UV water disinfector has a length of about 48 cm or less, a width of about 19.5 cm or less, and a height of about 15.75 cm or less.

18. The method of claim 15, wherein the UV lamp comprises a low pressure mercury lamp.

19. The method of claim 15, wherein the feed water delivery system is adapted to connect to a household tap.

20. The method of claim 15, wherein the feed water delivery system is adapted to connect to a holding tank.

* * * * *